United States Patent
Jeong et al.

(10) Patent No.: US 10,010,375 B2
(45) Date of Patent: Jul. 3, 2018

(54) SURGICAL ROBOT SYSTEM FOR REALIZING SINGLE-PORT SURGERY AND MULTI-PORT SURGERY AND METHOD FOR CONTROLLING SAME

(76) Inventors: Chang Wook Jeong, Seoul (KR); Hyung Tae Kim, Incheon (KR)

( * ) Notice: Subject to any disclaimer, the term of this patent is extended or adjusted under 35 U.S.C. 154(b) by 1162 days.

(21) Appl. No.: 13/699,852

(22) PCT Filed: Apr. 14, 2011

(86) PCT No.: PCT/KR2011/002659
§ 371 (c)(1),
(2), (4) Date: Feb. 7, 2013

(87) PCT Pub. No.: WO2011/149187
PCT Pub. Date: Dec. 1, 2011

(65) Prior Publication Data
US 2013/0144307 A1 Jun. 6, 2013

(30) Foreign Application Priority Data
May 25, 2010 (KR) .................... 10-2010-0048846

(51) Int. Cl.
*A61B 19/00* (2006.01)
*A61B 34/37* (2016.01)
(Continued)

(52) U.S. Cl.
CPC .............. *A61B 34/37* (2016.02); *A61B 34/30* (2016.02); *A61B 90/10* (2016.02); *B25J 9/0087* (2013.01);
(Continued)

(58) Field of Classification Search
CPC ........ B25J 9/0087; A61B 90/10; A61B 34/30; A61B 34/70; A61B 90/11; A61B 2017/00477; A61B 19/20; A61B 19/2203
(Continued)

(56) References Cited

U.S. PATENT DOCUMENTS

| 2006/0167440 A1* | 7/2006 | Cooper .............. A61B 19/2203 606/1 |
| 2006/0178559 A1 | 8/2006 | Kumar |
| 2008/0071289 A1 | 3/2008 | Cooper |

FOREIGN PATENT DOCUMENTS

| KR | 10-2005-0100147 A | 10/2005 |
| KR | 10-2010-0048789 A | 5/2010 |

OTHER PUBLICATIONS

International Search Report for the International Application No. PCT/KR2011/002659, Korean Intellectual Property Office, dated Dec. 26, 2011.

* cited by examiner

*Primary Examiner* — Katherine M Shi
(74) *Attorney, Agent, or Firm* — Dinsmore & Shohl LLP

(57) ABSTRACT

Provided is a surgical robot system for realizing single-port surgery and multi-port surgery, the system comprising: an operating device; and a controlling device for electro-mechanically controlling the operating device, wherein the operating device includes an alignment section having a plurality of main robot arms, and a plurality of manipulating sections each having a plurality of auxiliary robot arms, and in the multi-port surgery mode, the plurality of main robot arms and at least a portion of the plurality of auxiliary robot arms are operated so that each surgical tool coupled to each of the plurality of manipulating sections can be placed in correspondence with each of a plurality of incisions, and in the single-port surgery mode, the plurality of main robot arms and at least a portion of the plurality of auxiliary robot arms are operated so that each surgical tool coupled to each of the plurality of manipulating sections can be aligned in correspondence with one incision.

14 Claims, 9 Drawing Sheets

(51) Int. Cl.
  *A61B 34/30* (2016.01)
  *A61B 90/10* (2016.01)
  *B25J 9/00* (2006.01)
  *A61B 90/11* (2016.01)
  *A61B 34/00* (2016.01)
  *A61B 17/00* (2006.01)

(52) U.S. Cl.
  CPC .............. *A61B 34/70* (2016.02); *A61B 90/11* (2016.02); *A61B 2017/00477* (2013.01)

(58) Field of Classification Search
  USPC .............. 74/490.01, 490.05, 490.06, 490.07; 901/14–16, 19, 27–29
  See application file for complete search history.

SURGICAL ROBOT SYSTEM FOR REALIZING SINGLE-PORT SURGERY AND MULTI-PORT SURGERY AND METHOD FOR CONTROLLING SAME

PRIORITY

The present application claims priority under 35 U.S.C. § 371 to PCT Application PCT/KR2011/002659, filed on Apr. 14, 2011, which claims priority to Korean Patent Application No. 10-2010-0048846, filed on May 25, 2010, the disclosures of which are hereby incorporated by reference in their entireties.

FIELD OF THE INVENTION

This invention relates to a surgical robot system capable of implementing a single port surgery mode and a multi-port surgery mode and a method for controlling the same.

BACKGROUND

Minimally invasive surgery is a surgical approach that involves use of instruments inserted through several tiny incision openings to perform a surgery causing minimal tissue trauma.

This minimally invasive surgery relatively reduces changes in metabolism of the patient in the period of post-surgical care, so it is beneficial to rapid recovery of the patient. Therefore, using such minimally invasive surgery shortens length of a hospital stay of the patient after the surgery and allows patients to return to normal physical activities more quickly. In addition, minimally invasive surgery causes less pain and reduces scar to patients after surgery.

The most general form of the minimally invasive surgery is endoscopy. Among them, a laparoscopy that involves minimally-invasive inspection and operation inside abdominal cavity is known as the most general form of endoscopy. To operate the standard laparoscopic surgery, an abdomen of the patient is insufflated with gas, and small incisions (about ½ inch or less) are formed for use as an entrance of a tool for the laparoscopic surgery, through which a trocar is inserted. In general, laparoscopic surgical tools include a laparoscope (for observation of a surgical site) and other working tools. Here, the working tools are similar in structure to the conventional tools used for small incision surgery, except that the end effector or working end of each tool is separated from its handle by an elongated shaft. For instance, working tools may include a clamp, a grasper, scissors, a stapler, needle holder, and so forth. To perform the surgery, a user, such as a surgeon, puts the working tool into a surgical site through the trocar, and manipulates it from the outside of abdominal cavity. Then, the surgeon monitors the procedure of the surgery through a monitor that displays the image of the surgical site that is taken by the laparoscope. The endoscopic approach similar to this is broadly used in retroperitoneoscopy, pelviscopy, arthroscopy, cisternoscopy, sinuscopy, hysteroscopy, nephroscopy, cystoscopy, urethroscopy, pyeloscopy, and so on.

The modes for these minimally-invasive surgeries may be classified into the single port surgery mode and the multi-port surgery mode based on the number of ports to insert surgical instruments into the surgical field, etc.

When a surgery is performed in the multi-port surgery mode, the surgery may rather be easy despite of disadvantageous increasing number of incisions, on the other hand, when the surgery is performed in the single port surgery mode, the level of difficulty of the surgery may rise due to the problems such as collisions among the surgical instruments whereas the reduced number of incisions makes the surgery less invasive. In this context, the applicant of the invention has already disclosed minimally-invasive surgical instruments with multiple degrees of freedom in the Korean patent application No. 2008-51248 and No. 2008-61894, and the applicant has further disclosed the advantages of the single port surgery mode and minimally-invasive surgical instruments suitable for the same in the Korean patent application No. 2008-79126 and No. 2008-90560, the contents of which are incorporated herein by reference in its entirety.

Therefore, in case of real surgery, it is preferable to allow selectively implementing both of the single port surgery mode and the multi-port surgery mode according to various surgical situations in a single surgical robot system.

DETAILED DESCRIPTION

Technological Task

One object of the invention is to solve all problems in the conventional technology as described above.

Another object of this invention is to provide a surgical robot system capable of selectively implementing both of the single port surgery mode and the multi-port surgery mode and a method for controlling the same.

Technical Solution

Typical compositions of the invention to achieve the objects of the invention are as follows.

According to one aspect of the invention, a surgical robot system capable of implementing a single port surgery mode and a multi-port surgery mode, comprising a driving device; and a controlling device to control the driving device electro-mechanically, wherein the driving device comprises an alignment unit comprising multiple main robot arms and multiple operating units, each of which comprises multiple auxiliary robot arms, and wherein, in the multi-port surgery mode, at least some of the multiple main robot arms and the multiple auxiliary robot arms are driven so that each surgical instrument coupled with each of the multiple operating units can be disposed to each of multiple incisions, and in the single port surgery mode, at least some of the multiple main robot arms and the multiple auxiliary robot arms are driven so that each surgical instrument coupled with each of the multiple operating units can be aligned to a single incision is provided.

According to another aspect of the invention, a surgical robot system capable of implementing a single port surgery mode and a multi-port surgery mode, comprising a driving device; and a controlling device to control the driving device electro-mechanically, wherein the driving device comprises an alignment unit comprising multiple main robot arms and multiple operating units, each of which comprises multiple auxiliary robot arms, wherein the multiple main robot arms are comprised of a first main robot arm to move rotationally; a second main robot arm coupled with the first main robot arm to move rotationally; and a third main robot arm disposed to the second main robot arm to move rotationally, wherein the third main robot arm is coupled with the multiple operating units, wherein the multiple auxiliary robot arms are comprised of a first auxiliary robot arm to move rotationally; a second auxiliary robot arm coupled with the first auxiliary robot arm to move rotationally; and a third auxiliary robot arm disposed to the second main robot arm to move rotationally is provided.

Furthermore, other compositions to implement this invention may further be provided.

Effect of the Invention

According to the invention, a surgical robot system capable of selectively implementing both of the single port surgery mode and the multi-port surgery mode and a method for controlling the same is provided.

DETAILED DESCRIPTION OF THE INVENTION

Figure 1:
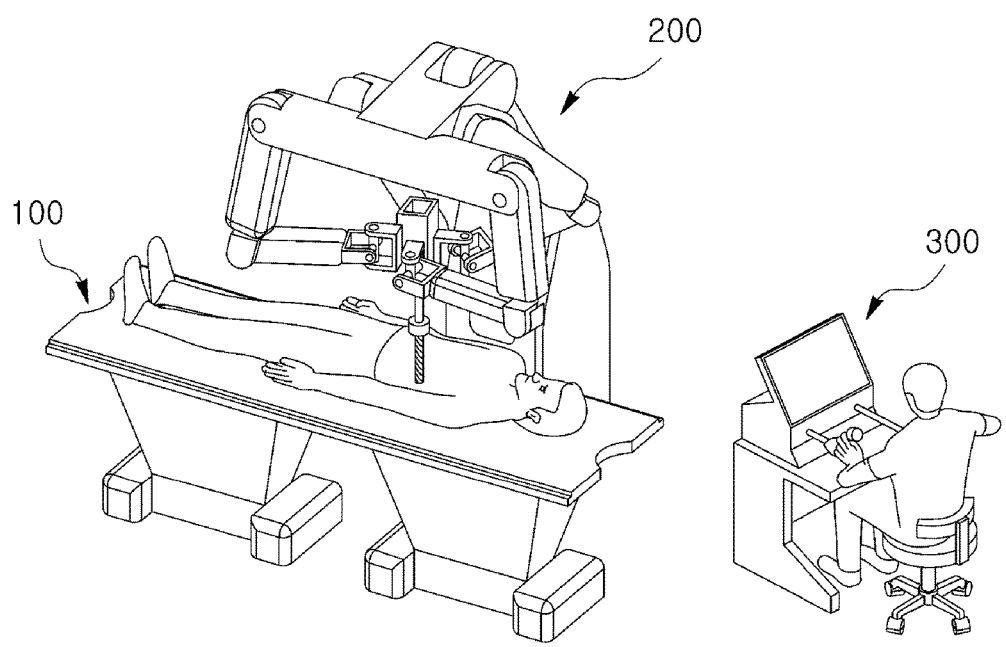
FIG. 1 shows an overall composition of a surgical robot system according to one embodiment of the invention.

Hereinafter, the present invention will be described in detail with reference to the accompanying drawings which illustrates particular embodiments of the invention. These embodiments are described specifically enough so that a person of ordinary skill in the art can perform the embodiments of the invention. It is to be understood that the various embodiments of the invention are different from each other but not necessarily exclusive to each other. For example, specific shapes, structures, characteristics described in this disclosure may be implemented as modified from one embodiment to another embodiment without departing away from the spirit and the scope of this invention. Furthermore, it shall be understood that the position or disposition of each element in each embodiment may also be modified without departing away from the spirit and the scope of the invention. Therefore, the detailed description in the following shall not be construed as limiting the present disclosure but falling into the whole scope of the claims and their equivalents. Same or similar elements are denoted by like reference numerals throughout the several aspects of the invention.

Hereinafter, a plurality of preferred embodiments of the present invention will be described in detail with reference to the accompanying drawings to be easily performed by a person of ordinary skill in the art.

[Preferred Embodiment of the Invention]
Composition of the Surgical Robot System In the following detailed description, the invention mainly describes the case presuming a laparoscopic surgery, however, it is not to be construed to limit the invention and it will be appreciated by a person of ordinary skill in the art that the surgical robot system or the method controlling the same according to the invention may be applied to any other type of surgery.

Furthermore, in the following detailed description, the number of the operating units 220 of the driving device 200 is presumed to be four for the description convenience, however, it is not to be construed to limit the invention, and it will be appreciated by a person of ordinary skill in the art that the invention can be applied in any case as long as it is according to the spirit of the invention and the number of the operating units 220 of the driving device 200 is two or more than 2.

FIG. 1 shows an overall composition of a surgical robot system according to one embodiment of the invention. With reference to FIG. 1, the surgical robot system may be composed comprising an operating table 100, a driving device 200 and a controlling device 300.

First, the operating table 100 according to one embodiment of the invention may be a device to support the body of a patient and to fix the body as necessary. This operating table 100 may comprise a frame structure firmly disposed against the floor or the ground to protect the patient from negative influence due to external vibration or impact. Preferably, the operating table 100 is disposed horizontally to the surface of the floor or the ground for more precise surgery. The operating table 100 can be, preferably, disposed parallel to each part of the third main robot arms described below.

Next, the driving device 200 according to one embodiment of the invention may be a device to drive surgical instruments directed to the patient on the operating table 100.

This driving device 200 may perform the function to align or dispose surgical instruments (e.g. minimally-invasive surgical instruments) to a certain position as necessary. For example, when the surgery is performed in the single port surgery mode, surgical instruments may be aligned to be disposed to one incision by the driving device 200. On the other hand, when a surgery is performed in the multi-port surgery mode, each of the multiple surgical instruments may be aligned to be disposed to different incisions. However, it shall be understood that the alignment or disposition of the surgical instruments according to the invention does not necessarily mean that the surgical instruments are to face the incision or the surgical instruments are to be inserted via the incision, but any motion for effective operation of the surgery are included in the alignments or dispositions of the surgical instruments according to the invention to align the multiple surgical instruments or dissemble the alignment thereof to perform both the single port surgery and the multi-port surgery by a single surgical robot system. In addition, when real surgery is performed, it shall be understood that users may introduce any manual operations for the alignment or disposition of the surgical instruments within a necessary range.

Furthermore, the driving device 200 may perform the surgery by driving aligned or disposed surgical instruments on the incision and by precisely controlling the same.

The driving device 200 as described above will be described in more detail below with reference to FIG. 2.

Finally, the controlling device 300 according to one embodiment of the invention may perform the function to control the driving device 200.

The controlling device 300 may control the driving device 200 by reflecting the operation of the user, and for this, for example, the controlling device 300 may comprise a user input tool such as a controlling lever, a keyboard, a mouse, a joystick and a pedal, and an electric signal generated by the operation of the user input tool by the user may be transmitted to the driving device 200. The electric signal transmitted to the driving device 200 may be used as the input signal to operate each element comprised in the driving device 200 by electro-mechanical driving tools such as an electric motor (not shown) or a hydraulic cylinder (not shown). That is, the controlling device 300 may control the motion of each element electro-mechanically. Particularly, the Korean Patent Application No. 2008-108103 filed by the same applicant discloses an embodiment on the motion controlling of each element of the driving device 200, the content of which is incorporated herein by reference by its entirety.

The controlling device 300 is a digital device comprising the function enabling the user to control the driving device 200 and any digital device containing memorizing tool and microprocessor with calculation function may be adopted as the controlling device of the invention.

However, it shall be understood that the controlling device (300) of the present invention does not necessarily control every element of the driving device 200 but at least some elements of the driving device 200 may be manually controlled by the user.

Composition of the Driving Device 200

Hereinafter, the composition and the function of each element of the driving device 200 which perform important functions to implement the invention will be described.

Embodiment I

Figure 2:
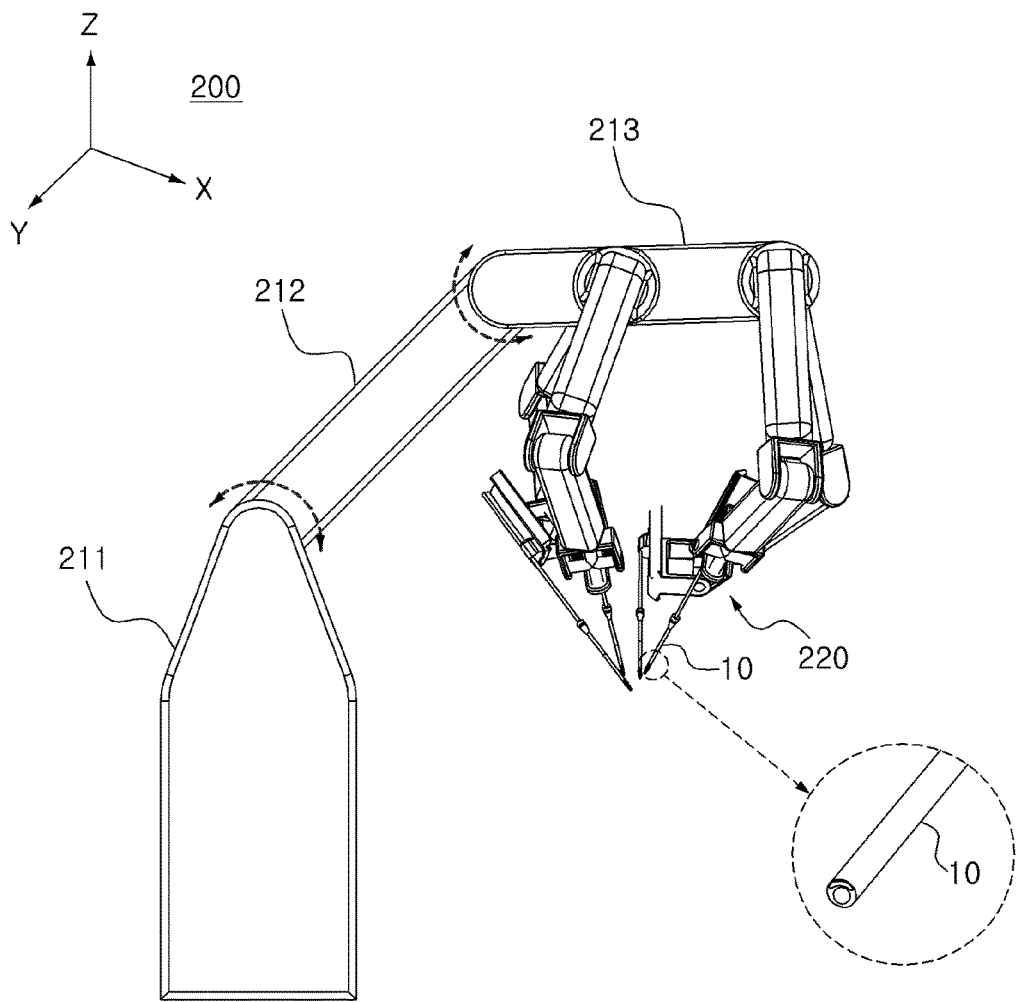
FIGS. 2 to 4 show a lateral view, a perspective view, an exploded perspective view of the driving device 200 according to the Embodiment I of the invention.
Figure 3:
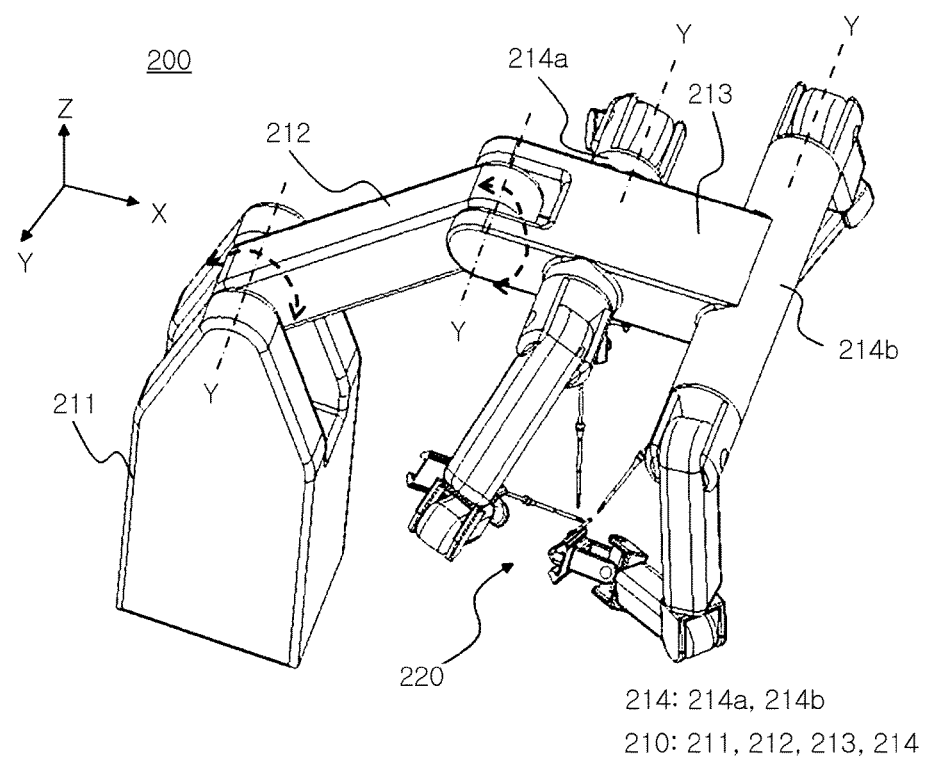
Figure 4:
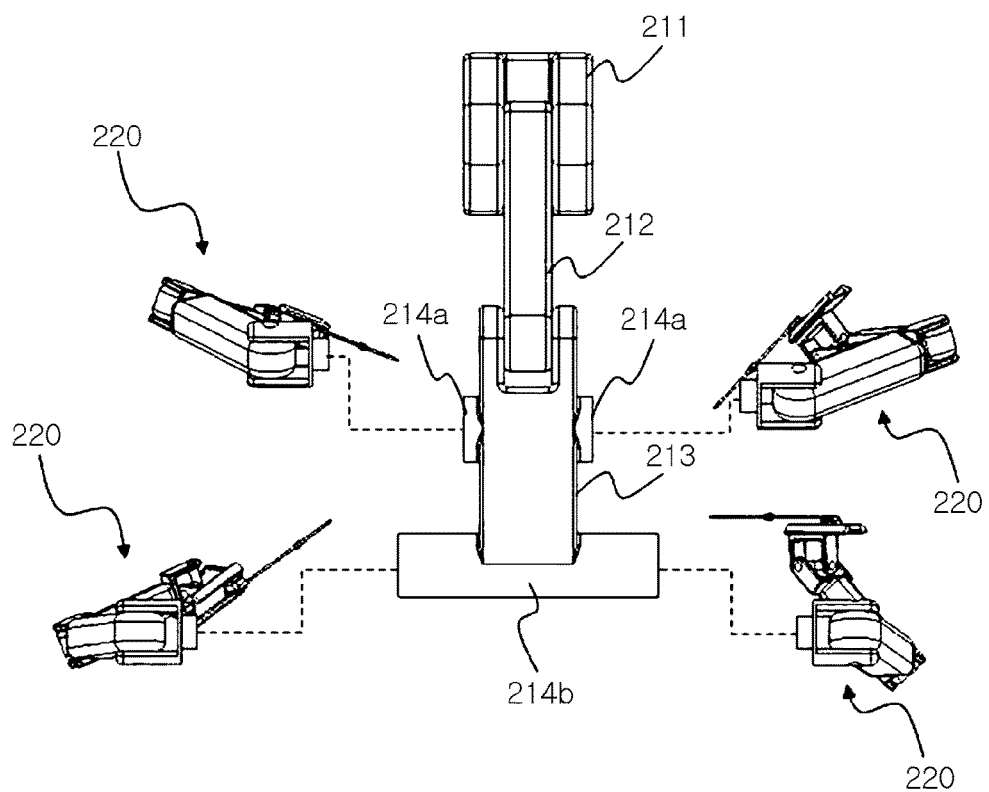

FIGS. 2 to 4 show a lateral view, a perspective view, and an exploded perspective view of the driving device 200 according to the Embodiment I of the invention. First, with reference to FIGS. 2 to 4, the driving device 200 according to the Embodiment I of the invention comprises the alignment unit 210 and operating unit 220.

First, the alignment unit 210 may function to align or dispose the surgical instrument 10 at the suitable position to operate a surgery to the patient on the operating table 100 depending on the surgical mode. Here, the surgical instrument 10 may be an endoscope or a minimally-invasive surgical instrument as shown in FIG. 2. Specific composition of the surgical instrument 10 will be described below with reference to FIG. 5. However, it shall be understood that any surgical instrument 10 illustrated or described as a minimally-invasive surgical instrument comprising a working end capable of open-and-close motion for the convenience of illustration and description herein, may be substituted with an endoscope or any other minimally-invasive surgical instrument chosen by the user.

The alignment unit 210 may comprise a main support unit 211, a first main robot arm 212, a second main robot arm 213 and a third main robot arm 214.

First, it is preferred that the main support unit 211 is configurated as the entire driving device 200 may not be affected from any external vibration or impact for a smooth progress of the surgery. To achieve this, the main support unit 211 is made of high-load material so that it may be firmly fixed on the floor or the ground.

On the other hand, each end of the first main robot arm 212 and the main support unit 211 are coupled to each other, so that the first main robot arm 212 may move rotationally as shown, for example, in a pitch direction, rotating about Y-axis.

Furthermore, each end of the second main robot arm 213 and the first main robot arm are also coupled to each other, so that the second main robot arm 213 may move rotationally as shown, for example, in a pitch direction, rotating about Y-axis.

Furthermore, the third main robot arm 214 as shown is disposed substantially orthogonal to the second main robot arm 213 to move rotationally in the direction as shown, for example, rotating in a pitch direction about Y-axis. The two parts 214a and 214b of the above third main robot arm 214 may move rotationally independent from each other. And according to the drawings, the part 214a and the part 214b of the third main robot arm 214, respectively, may be equipped to other short parts of the second main robot arm 213 located near and across the joint between the short part of the second main robot arm 213 and the short part of the first main robot arm 212. One operating unit 220 may be coupled to each of the four short parts of the part 214a and 214b of the third main robot arm 214, respectively (Particularly, FIG. 4 clearly shows such coupling). These operating units 220 may move rotationally about Y-axis of the third main robot arm 214. On the other hand, it may be preferred to adjust the length of the part 214a and the part 214b of the third main robot arm 214 to be different from each other as shown. This may allow each operating unit 220 to utilize different spaces (rotation spaces) from each other. The main robot arms (212 to 214) and the operating unit 220 will be described in detail below with reference to FIG. 5.

Figure 5:
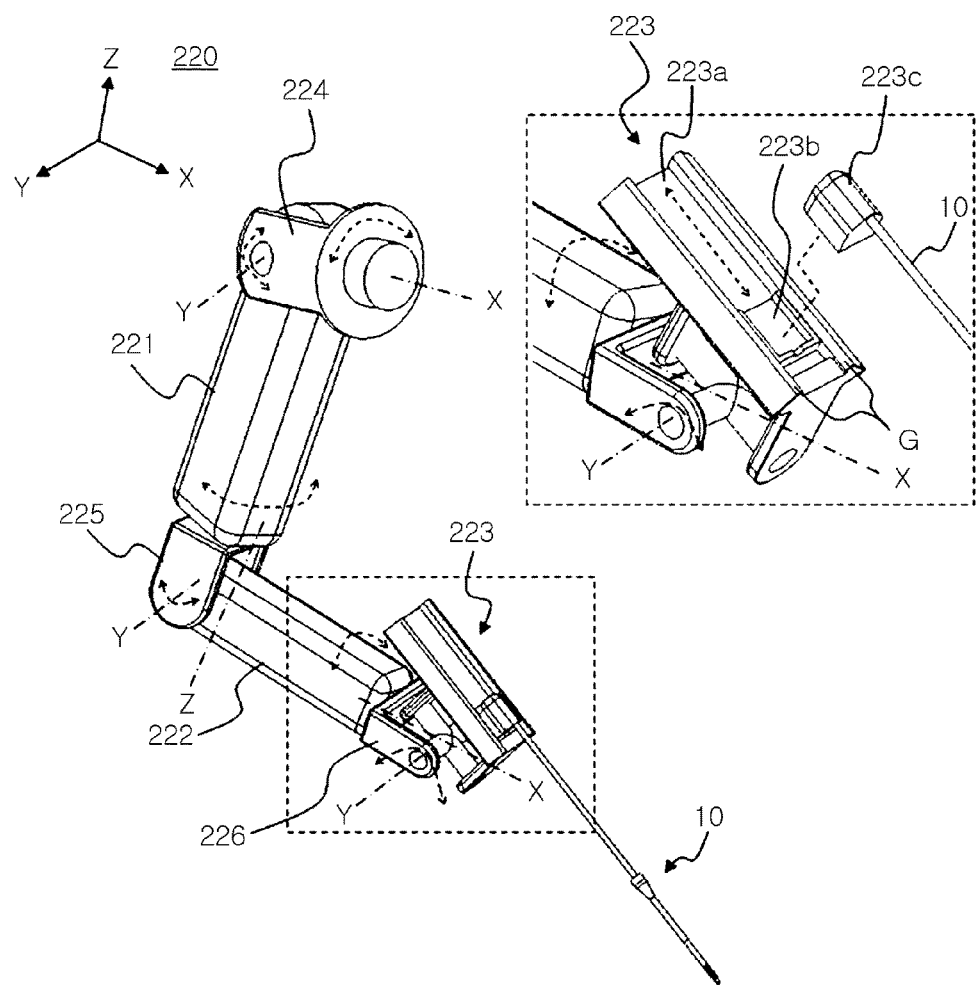
FIG. 5 shows the composition of the operating unit 220 of the driving device 200 according to the Embodiment I of the invention.

FIG. 5 shows the composition of the operating unit 220 of the driving device 200 according to the Embodiment I of the invention. As described above, this operating unit 220 is coupled to the third main robot arm 214 to perform the function to align/dispose and precisely control the surgical instrument 10.

As shown in FIG. 5, the operating unit 220 may comprise auxiliary robot arms such as a first auxiliary robot arm 221, a second auxiliary robot arm 222 and a third auxiliary robot arm 223, and joint units such as a first joint unit 224, a second joint unit 225 and a third joint unit 226.

First, one end of the first auxiliary robot arm 221 is coupled with the third main arm 214 by the first joint unit 224 so that the first auxiliary robot arm 221 may move rotationally about X-axis and Y-axis. Rotating directions of this case are yaw direction and pitch direction.

Then, one end of the second auxiliary robot arm 222 is coupled with the other end of the first auxiliary arm 211 by the second joint unit 225 so that the second auxiliary robot arm 222 may move rotationally about Y-axis and Z-axis. Rotating directions of this case are pitch direction and roll direction.

Finally, one end of the third auxiliary robot arm 223 is coupled with the other end of the second auxiliary arm (212) by the third joint unit 226 so that the third auxiliary robot arm 223 may move rotationally about X-axis and Y-axis. Rotating directions of this case are roll direction and pitch direction.

On the other hand, as described above, it may be preferred for the first auxiliary robot arm 221 to the third auxiliary robot arm 223 to have a motion range of 180 degrees or more in the Y-axis rotation. Furthermore, in such case, the motion ranges of the first auxiliary robot arms 221 of the operating units 220 respectively coupled to both ends of a single third main robot arm 213 are preferably symmetric to each other (Such symmetric rotational motion ranges may provide more intuition to the user to understand the motion of the operating unit 220 or the surgical instrument 10.

On the other hand, as described above, the third auxiliary robot arm 223 may be comprised of a body 223*a*, a moving unit 223*b* and a holding unit 223*a* as shown in the enlarged perspective view.

The body 223*a* is coupled with the third joint unit 226 to move rotationally about Y-axis (i.e. rotation in pitch direction). And the moving unit 223*b* may be coupled with the body 223*a* by a guide G formed on one surface of the body 223*a* in a sliding manner to move in surge direction. Furthermore, the holding unit 223*a* may perform the function to fix a certain surgical instrument 10 to the moving to unit 223*b*.

The surgical instrument 10 as described above may include an endoscope and/or a minimally-invasive surgical instrument using the mechanism disclosed in the Korean Patent Application No. 2008-51248 or No. 2008-61894 or an endoscope or a minimally-invasive surgical instrument disclosed in the Korean Patent Application No. 2008-108103. Such surgical instrument 10 is coupled with the driving device 200 according to the Embodiment I, so that at least one of surge direction motion, pitch direction motion, yaw direction motion, roll direction motion and the open-and-close motion of the working short part of the surgical instrument 10 by the control signal from the controlling device 300 and/or the manual control by the user may be performed.

Embodiment II

The composition of the driving device 200 according to the Embodiment II of the invention is basically same as the driving device 200 according to the Embodiment I. However, since some key differences exist, emphasis will be on the differences below.

Figure 6:
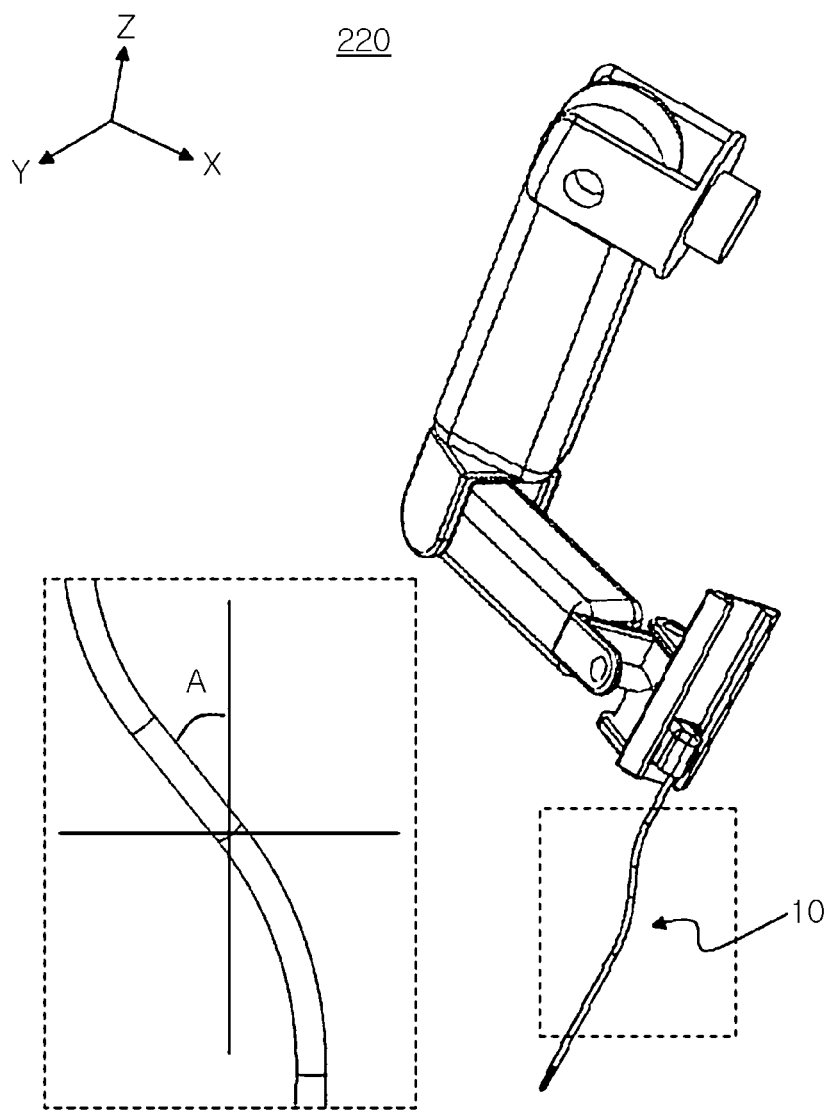
FIG. 6 shows the composition of the operating unit 220 of the driving device 200 according to the Embodiment II of the invention.

FIG. 6 shows the composition of the operating unit 220 of the driving device 200 according to the Embodiment II of the invention.

With reference to FIG. 6, the surgical instrument 10 coupled with the operating unit 220 of the driving device 200 according to the Embodiment II of the invention spontaneously form a certain angle A and have a curvature. The curvature may be preformed by cutting-and-bending of at least one shaft or be formed later by the control of the user, and when the surgery is performed in the single port surgery mode, such curvature may secure a room to observe surgery area among multiple surgical instruments 10, and the short parts of the multiple surgical instrument 10 may be placed in a smaller area so that the small incision may be sufficient. Furthermore, due to the curvature, the effect that the surgery assistant of the user can easily insert the necessary surgical instrument into the surgery area can be achieved.

The surgery mode of the overall surgical robot system will be described more hereinafter.

Figure 7:
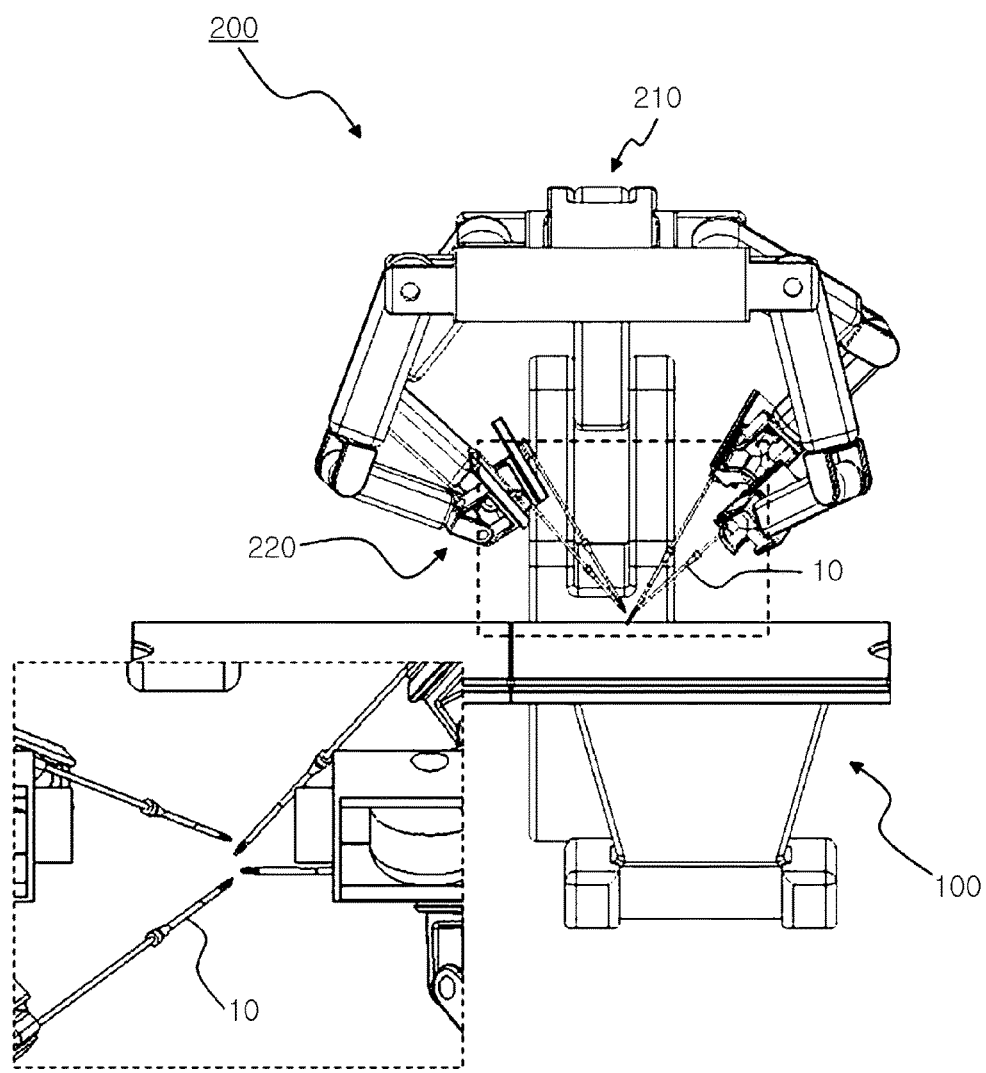
FIG. 7 shows an operating example of the driving device 200 in the multi-port surgery mode according to the Embodiment I of the invention.

FIG. 7 shows an operating example of the driving device 200 in the multi-port surgery mode according to the Embodiment I of the invention.

With reference to FIG. 7, if the driving device 200 according to the Embodiment I operates in the multi-port surgery mode by the control signal from the controlling device 300 and/or the manual operation by the user, each surgical instrument 10 of the four operating units 220 may be driven to be disposed toward the surgery area via different incisions. Therefore, according to the invention, multi-port surgery may be easily performed.

Figure 8:
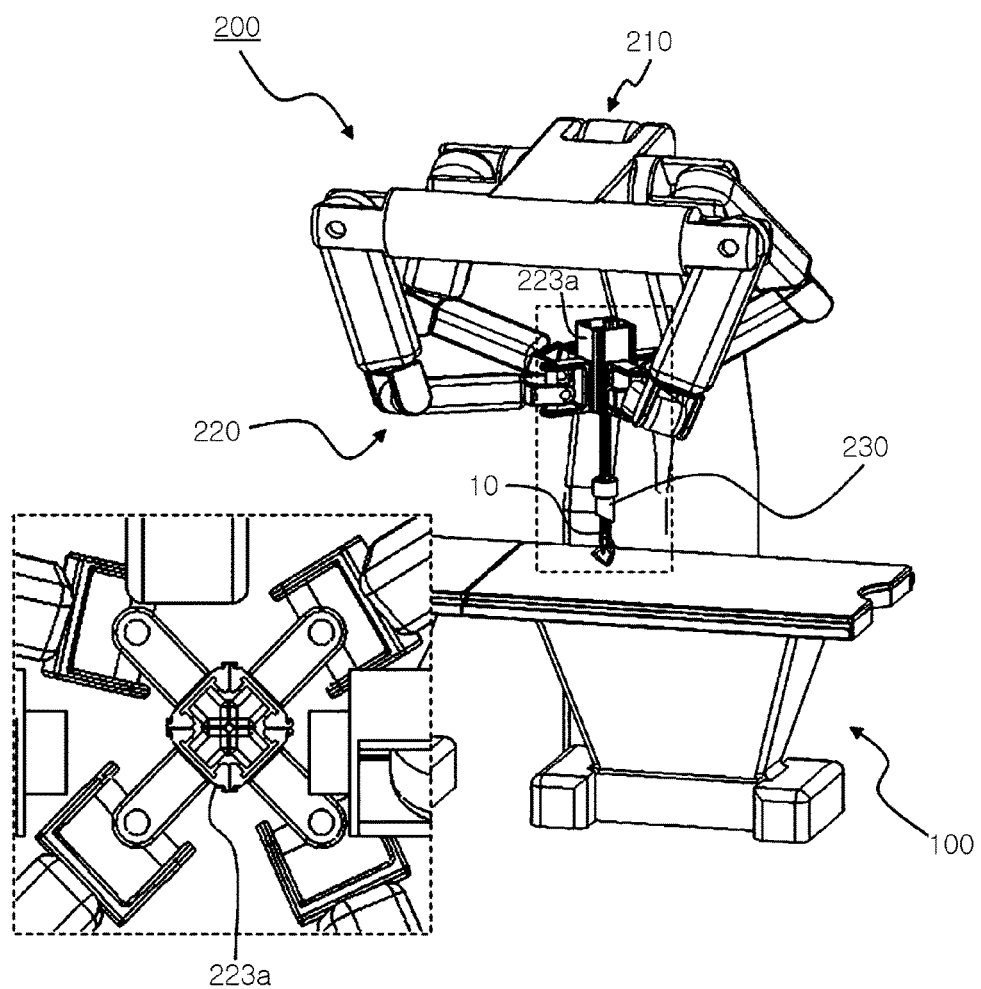
FIG. 8 shows an operating example of the driving device 200 in the single port surgery mode according to the Embodiment I of the invention.

FIG. 8 shows an operating example of the driving device 200 in the single port surgery mode according to the Embodiment I of the invention.

With reference to FIG. 8, if the driving device 200 according to the Embodiment I operates in the single port surgery mode by the control signal from the controlling device 300 and/or the manual operation by the user, each surgical instrument 10 of the four operating units 220 may be driven to be aligned toward the surgery area via the same incision. In this case, each of the four third auxiliary robot arms 223, as shown in the enlarged perspective view, may be aligned so that one edge of the body 223*a* may meet the edge of the another body 223*a*. In this case, four bodies 223*a*, from a top view, as shown in the enlarged perspective view, may form a quadrangle shape (Such shape may depend on the number of the operating units 220 of the surgical robot system; for example, the shape may be hexagonal when the six operating units exist). Therefore, according to the invention, the surgical instrument 10 fixed on each of the four holding units 223*c* corresponding to the four bodies 223*a* may be easily aligned, so that the multiple surgical instruments 10 may be inserted via the single incision together. The aligned structure, in the single port surgery mode, enhances the mechanical stability of the surgical instrument 10, and fixes the relative position of the surgical instruments 10 to each other for the easier control of the surgical instruments 10.

On the other hand, according to one embodiment of the invention, to achieve high stability in the single port surgery mode, extra port for single port surgery 230 may further be used as shown in FIG. 8. (The Korean patent application No. 2008-99872 of the applicant discloses a specific composition of a port for the single port surgery, the content of which is incorporated herein by reference in its entirety). Such port for the single port surgery 230 may perform the function to fix the multiple surgical instruments 10 within one bundle.

On the other hand, when the single port surgery is performed instead of the multi-port surgery mode described with reference to FIG. 7, it is preferred to utilize the surgical instruments 10 having the elbow mechanism disclosed in the Korean Patent Application No. 2008-79126 or No. 2008-90560 (Korean patent application No. 2008-108103 further discloses the utilization of the surgical instrument 10). When single port surgery is performed with these surgical instruments 10, a certain fixed fulcrum may be required so that the multiple surgical instruments 10 inserted via the single incision (single port) may act as a single unit (For example, in case of a laparoscopic surgery, a point where the abdominal wall and the hypothetical axis of centered among the longitudinal axes of the surgical instruments 10 meet each other may be presumed as the fulcrum). And the fulcrum may be included in the port for the single port surgery as described above. Based on the fulcrum, multiple surgical instruments 10 can be controlled to be operated in pitch direction, yaw direction, roll direction and/or surge direction as one unit. (For this, it is preferable for the multiple surgical instruments 10 to be aligned to each other at least at the fulcrum). In this case, it is obvious that each of multiple surgical instrument 10, can spontaneously move in the roll and/or surge direction or perform the joint motion when each instrument fixed on the corresponding third auxiliary robot arm 223.

Figure 9:
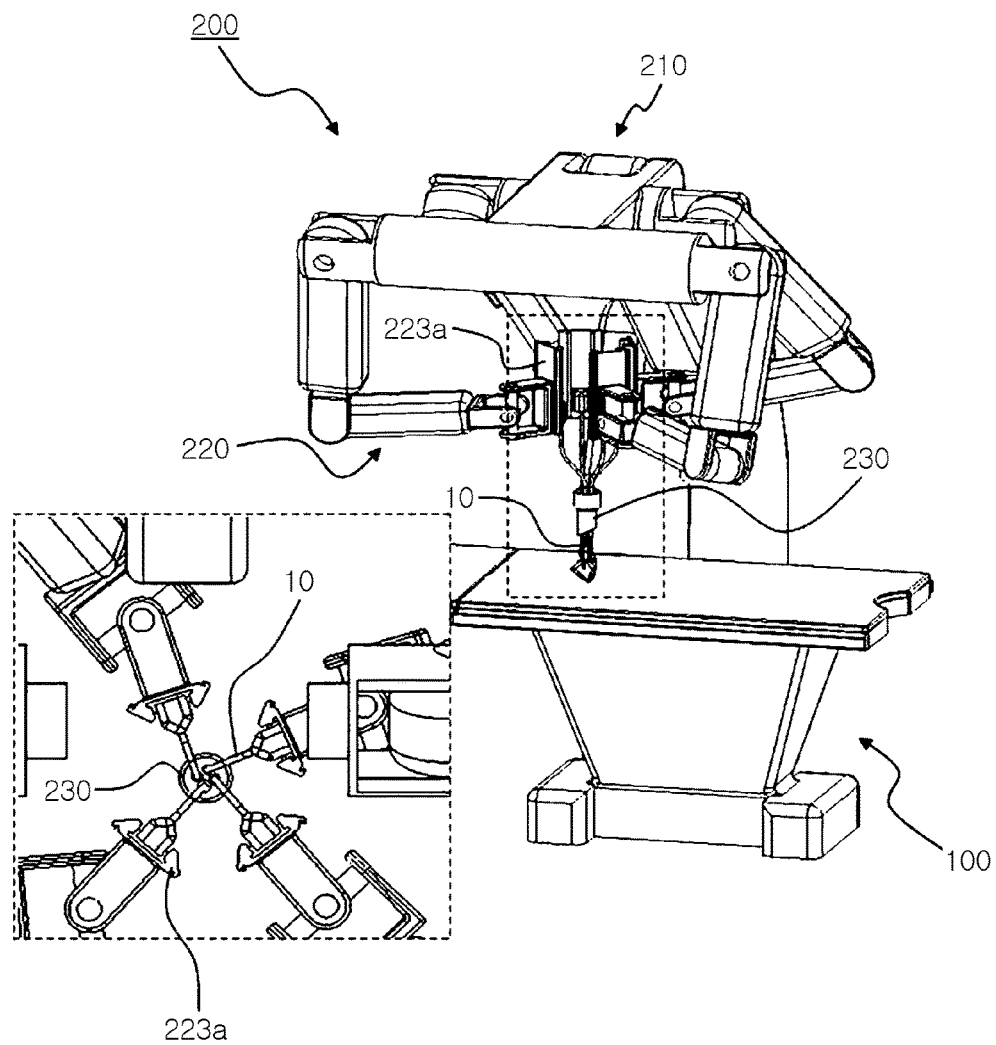
FIG. 9 shows an operating example of the driving device 200 in the single port surgery mode according to the Embodiment II of the invention.

FIG. 9 shows an operating example of the driving device 200 in the single port surgery mode according to the Embodiment II of the invention.

With reference to FIG. 9, the shafts of the four surgical instruments 10 disposed to the four operating units 220 are controlled to have the curvature to be away from the corresponding first auxiliary robot arm 221 and the second auxiliary robot arm 222 (it is obvious that such curvature may be preformed in the surgical instruments 10 as described above). The Korean patent application No. 2008-

79126 and No. 2008-90560 disclose the control of the shaft of the surgical instrument 10.

On the other hand, it is obvious that the port for the single port surgery 230 as described above can also be used in the case shown in FIG. 9.

Although explanatory description is provided with particular features such as specific elements, limited embodiments and drawings, it is to help the more inclusive understanding of the invention and shall not be construed to limit the invention, and it will be appreciated by a person of ordinary skill in the art that various modifications and changes can be made from the description.

Therefore, the spirit of the present invention shall not be limited to the embodiment described above, and the claims below and their equivalents or any equivalent changes will fall into the scope of the spirit of the invention.

What is claimed is:

1. A surgical robot system for implementing a single port surgery mode and a multi-port surgery mode, comprising:
   a driving device; and
   a controlling device to control the driving device electromechanically,
   wherein the driving device comprises:
   an alignment unit comprising a plurality of main robot arms; and
   a plurality of operating units, wherein each of the plurality of operating units comprises a plurality of auxiliary robot arms,
   wherein the plurality of main robot arms comprise:
   a first main robot arm to move rotationally;
   a second main robot arm coupled with the first main robot arm to move rotationally; and
   a third main robot arm coupled with the plurality of operating units and disposed at the second main robot arm to move rotationally,
   wherein the plurality of auxiliary robot arms comprise:
   a first auxiliary robot arm to move rotationally;
   a second auxiliary robot arm coupled with the first auxiliary robot arm to move rotationally; and
   a third auxiliary robot arm disposed at the second main robot arm to move rotationally, and
   wherein, in the multi-port surgery mode, at least some of the plurality of main robot arms and the plurality of auxiliary robot arms are driven so that a plurality of surgical instruments, each of which is coupled with each of the plurality of operating units, are disposed with respect to a plurality of incisions;
   in the single port surgery mode, at least some of the plurality of main robot arms and the plurality of auxiliary robot arms are driven so that each of the plurality of surgical instruments coupled with each of the plurality of operating units is disposed with respect to a single incision, and at least two of the plurality of surgical instruments act as a single unit based on a predetermined fulcrum, wherein at least two of the plurality of surgical instruments are aligned to be substantially parallel to each other at least at the fulcrum; and
   the surgical robot system further comprises a port for single port surgery for enabling at least two of the plurality of surgical instruments to act as a single unit, wherein the fulcrum is included in the port for single port surgery.

2. A surgical robot system as claimed in claim 1,
   wherein the controlling device comprises at least one of a controlling lever, a keyboard, a mouse, a joystick and a pedal.

3. A surgical robot system as claimed in claim 1,
   wherein the first main robot arm is configured to move rotationally in a pitch direction;
   the second main robot arm is configured to move rotationally in a pitch direction, one end of the second main robot arm being coupled with the first main robot arm; and
   the third main robot arm is configured to move rotationally in a pitch direction, the third main robot arm being substantially orthogonally disposed at the second main robot arm.

4. A surgical robot system as claimed in claim 1,
   wherein the first auxiliary robot arm is configured to move rotationally in pitch and yaw directions;
   the second auxiliary robot arm is configured to move rotationally in pitch and roll directions, one end of the second auxiliary robot arm being coupled with the first main robot arm; and
   the third auxiliary robot arm is configured to move rotationally in pitch and roll directions, one end of the third auxiliary robot arm being coupled with the second main robot arm.

5. A surgical robot system as claimed in claim 1,
   wherein the third main robot arm comprises a plurality of parts different from each other in length.

6. A surgical robot system as claimed in claim 5,
   wherein the rotational movement ranges of the first auxiliary robot arms of two opposing operating units, which are coupled to one of the plurality of parts, are symmetrical to each other.

7. A surgical robot system as claimed in claim 1,
   wherein at least two of the plurality of third auxiliary robot arms are aligned to be substantially parallel to each other.

8. A surgical robot system as claimed in claim 1,
   wherein the third auxiliary robot arm comprises:
   a body coupled with the second auxiliary robot arm;
   a moving unit to move with reference to the body in a surge direction; and
   a holding unit to fix a surgical instrument to the moving unit.

9. A surgical robot system as claimed in claim 8,
   wherein, in the single port surgery mode, an edge of the body of one of the third auxiliary robot arms adjoins an edge of the body of another third auxiliary robot arm.

10. A surgical robot system as claimed in claim 1,
    wherein each of the plurality of surgical instruments is an endoscope or a minimally-invasive surgical instrument.

11. A surgical robot system as claimed in claim 10,
    wherein each of the plurality of surgical instruments has curvature.

12. A surgical robot system as claimed in claim 11,
    wherein the curvature is formed in a direction to separate the working end of each of the plurality of surgical instruments from the corresponding first auxiliary robot arm and the corresponding second auxiliary robot arm.

13. A surgical robot system as claimed in claim 1,
    wherein the fulcrum is set on a point where an abdominal wall meets a virtual central axis of the vertical axes of the plurality of surgical instruments.

14. A method for controlling the surgical robot system as claimed in claim 1, comprising:
    a step of controlling at least one of the plurality of surgical instruments to have curvature, in the single port surgery mode.

* * * * *